United States Patent [19]
Cullimore et al.

[11] Patent Number: 4,906,566
[45] Date of Patent: Mar. 6, 1990

[54] METHOD AND APPARATUS FOR PRODUCING ANALYTIC CULTURE

[76] Inventors: D. Roy Cullimore, 2003 Styles Crescent, E., Regina, Saskatchewan, Canada, S4V 0P8; George W. Alford, 1954 Old Daytona Rd., Daytona Beach, Fla. 32014

[21] Appl. No.: 182,224

[22] Filed: Apr. 15, 1988

[51] Int. Cl.$^4$ .......................... C12Q 1/04; C12Q 1/24; C12M 1/24; C12M 1/16

[52] U.S. Cl. ........................................ 435/34; 435/30; 435/296; 435/299; 435/311; 435/801

[58] Field of Search ...................... 435/30, 34, 32, 296, 435/312, 801, 810, 818, 311, 299, 243; 422/102; 436/69; 261/120, 92

[56] References Cited

U.S. PATENT DOCUMENTS

| | | | |
|---|---|---|---|
| 4,276,383 | 6/1981 | Leighton et al. | 435/291 |
| 4,278,437 | 7/1981 | Haggar | 436/69 X |
| 4,299,918 | 11/1981 | Popoff et al. | 435/34 X |
| 4,320,087 | 3/1982 | Chan et al. | 422/102 X |
| 4,494,581 | 1/1985 | Gordon | 422/102 X |
| 4,717,660 | 1/1988 | Schulte | 435/30 |

OTHER PUBLICATIONS

Finegold et al, Bailey and Scotti Diagnostic Microbiology, C. V. Mosby Co., St. Louis, (1978), p. 450.

Primary Examiner—Randall E. Deck
Attorney, Agent, or Firm—James B. Middleton

[57] ABSTRACT

A testing device allows field tests to determine the presence of microorganisms in a given fluid. A container may have a culture medium in dry form, and a floatable device in the container. When a liquid sample is placed into a container, the floatable device floats on the surface and intercedes the exchange of oxygen from the atmosphere to the liquid. An oxygen content sufficient for aerobes is provided at the surface of the liquid, a reduced oxygen content for microaerobes provided just below the intercedent device, and no-oxygen content for anaerobes is provided at the bottom of the container. Selection of the culture medium can assist in detecting specific organisms, and further information can be gained by observing colorations, gas bubbles, precipitates and the like.

9 Claims, 1 Drawing Sheet

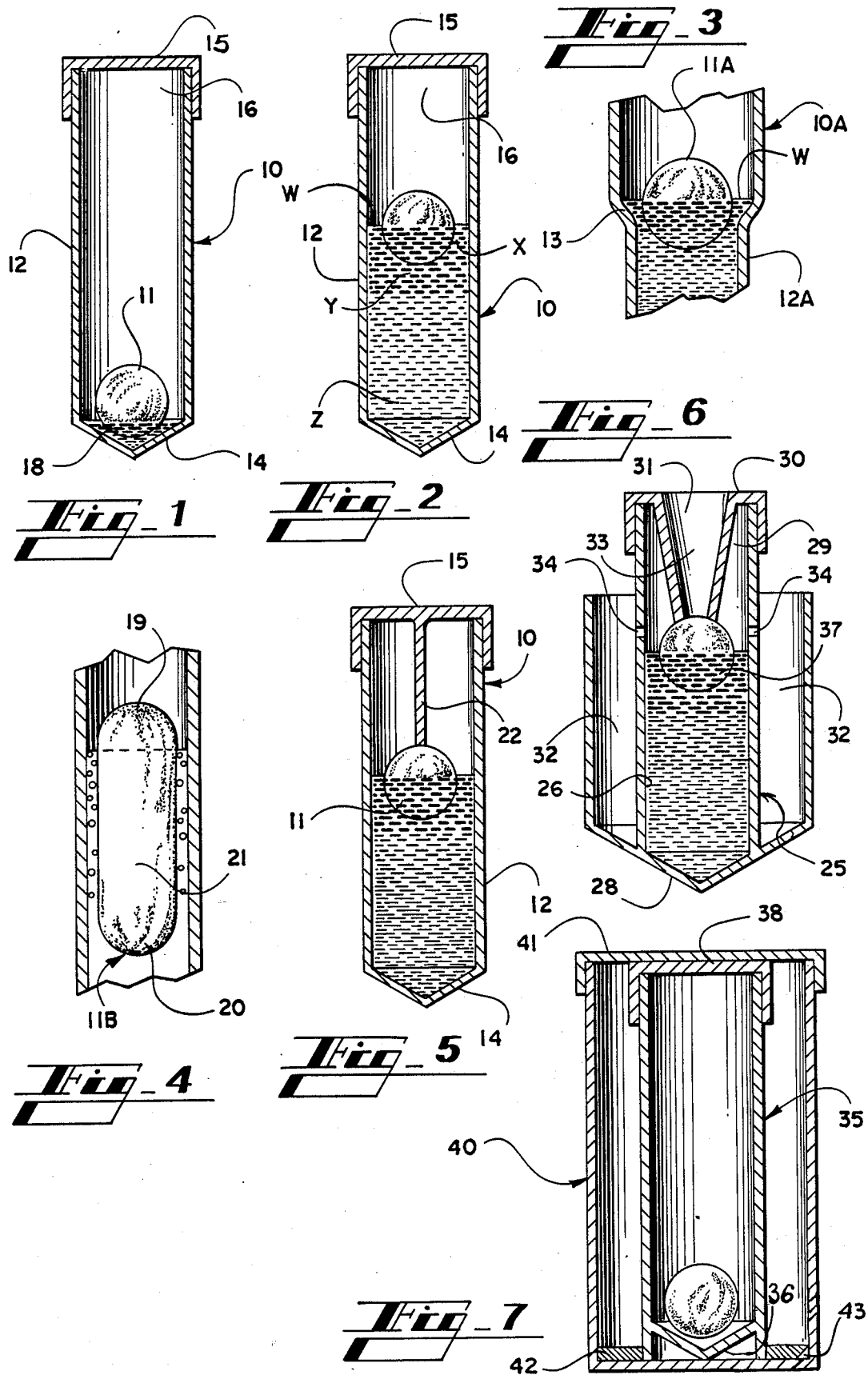

METHOD AND APPARATUS FOR PRODUCING ANALYTIC CULTURE

INFORMATION DISCLOSURE STATEMENT

Recent advances in microbiology have engendered many laboratory techniques useful to the engineer, microbiologist and various health specialists. A large number of tests is conducted daily, both in the field and in the laboratory. With the increasing awareness of potential sources of infection, there is a greater and greater demand for screening of substances, notably of water to be used for drinking. However, due to the time required for the tests and the cost of many tests, complete testing is not economically feasible so that tests may be run only on substances already under suspicion due to various observable evidence.

Those skilled in the art will realize that an incipient problem may not manifest itself in the natural state for one or more of various reasons, but the contamination may become obvious after some interference in the natural system. By way of example, bacteria may be present in small quantities, but not apparent due to lack of proper environment for growth of the bacteria. In such situations, the manipulation of the environment may well introduce the necessary ingredient to cause the rapid growth of the bacteria and consequent contamination beyond acceptable levels. It is known, for example, that aerobic bacteria may lie in a dormant state due to lack of oxygen. Manipulation of the environment, then, may introduce sufficient oxygen to create a bacterial contamination that is of concern.

The prior art includes some culture systems for growing bacterial cultures, and the prior art includes the concept of utilizing a physical device to separate an oxygen-rich environment from an oxygen-poor environment. The prior art does not include a complete test device for use in the field to provide adequate screening of samples of substances to determine contamination or incipient contamination.

SUMMARY OF THE INVENTION

This invention relates generally to a method and apparatus for performing microbiological analysis, and is more particularly concerned with culture means for screening a sample quickly to determine approximate microbiological loadings in the sample.

The present invention provides a method whereby a sample of material can be placed into a test device, and one test can determine the presence or absence of aerobic, microaerobic and/or anaerobic material. By selection of the culture medium and the size and shape of an intercedent device, more detailed analysis of the particular bacteria can be made.

The present invention provides a test chamber having a floatable intercedent device which physically restricts fluid flow in the test chamber; and, the intercedent device in conjunction with the activity of the aerobic bioforms, restricts oxygen flow into the test chamber below the intercedent device sufficiently to provide an oxygen gradient. The result is that aerobic bacteria may grow substantially at the air-medium interface, microaerobic bacteria may grow somewhat below the interface, and anaerobic bacteria may grow far down in the test chamber.

BRIEF DESCRIPTION OF THE DRAWINGS

These and other features and advantages of the present invention will become apparent from consideration of the following specification when taken in conjunction with the accompanying drawings in which:

FIG. 1 is a diametrical cross-sectional view of a culture chamber made in accordance with the present invention, and having a concentrated culture medium therein;

FIG. 2 is a view similar to FIG. 1, but showing the device after addition of a liquid sample;

FIG. 3 is a fragmentary, detailed view showing a modified chamber wall structure;

FIG. 4 is a fragmentary, detailed view similar to FIG. 3 showing a modified form of intercedent device;

FIG. 5 is a view similar to FIG. 2 showing a slightly modified form of the device;

FIG. 6 is a longitudinal, cross-sectional view showing another modified form of the test chamber; and, FIG. 7 is a longitudinal, cross-sectional view showing the test chamber of FIGS. 1 and 2 within an additional, sterilization chamber.

DETAILED DESCRIPTION OF THE EMBODIMENTS

Referring now more particularly to the drawings, and to those embodiments of the invention here presented by way of illustration, it will be seen that the present invention includes a test chamber 10 having a floatable intercedent device 11 within the chamber 10.

The rationale of the present invention is to provide a device having a variety of environments. The environments differ primarily in oxygen concentration, and secondarily in availability of surface for microbial attachment and subsequent sessile growth. Both these environmental factors are achieved somewhat through the use of the intercedent device 11, and the complete mechanism will be discussed in more detail below.

Looking specifically at FIG. 1 of the drawings, it will be noted that the test chamber 10 is of a generally cylindrical shape, though the walls 12 may slope inwardly somewhat to create a frustoconical shape. The base angle of the cone is preferably approaching 90°, so that the container appears to be substantially cylindrical. The bottom 14 of the container 10 is preferably conical as shown, and a cap 15 selectively closes the open end 16 of the test chamber 10.

The floatable intercedent device 11 is within the chamber 10, and normally rests at the conical bottom 14 as shown. It is contemplated that the test chamber of the present invention will be shipped and stored in the form shown in FIG. 1, and it will, be understood that, conveniently, a selected culture medium can be placed in the chamber 10 as indicated at 18. It is known that such culture media are available in dried, pelletized form, and need only to have water added in order to have an active culture medium. The test chamber 10 shown in FIG. 1 is also shown in FIG. 2, and it will be seen that water or other liquid has been added to the test chamber 10 so that the intercedent device 11 floats generally at the surface of the liquid.

Looking further at FIG. 2 of the drawings, it will be seen that the intercedent device 11 is generally spherical, so that the space between the intercedent device 11 and the wall 12 of the test chamber 10 is relatively small. This physical restriction assists in reducing the oxygen flow into the liquid, and it will of course be noted that a significant surface area is provided on the intercedent device 11 immersed in the liquid. A natural result of this arrangement is that sessile material has adequate surface on which to grow, and of course planktonic forms can grow within the liquid, below the device 11.

Looking at FIG. 3 of the drawings, it will be seen that the intercedent device indicated at 11A is within a test chamber designated at 10A. In FIG. 3, the wall 12A of the test chamber 11A is stepped outwardly to provide a shelf 13 so that the surface of the liquid is at a point above the shelf for providing a greater area exposed to the air. Such an increased area will allow greater oxygen content to promote the growth of aerobic bacteria.

Looking at FIG. 4 of the drawings, the intercedent device is indicated at 11B, and it will be seen that the device 11B is vertically elongated, having hemispherical ends 19 and 20 and generally cylindrical midportion 21. A complete understanding of the operation of the intercedent device 11B will be had from consideration of the discussion below.

Looking next at FIG. 5 of the drawings, the test chamber is again indicated at 10, and the intercedent device is indicated at 11. Other parts of the arrangement shown in FIG. 5 carry the same reference numerals as the device shown in FIGS. 1 and 2.

The one difference in the apparatus shown in FIG. 5 of the drawings is the use of a level gauge or indicating device 22 extending from the cap 15 to the intercedent device 11. Though many forms of level gauge or the like may be utilized, the gauge 22 can easily be formed as a part of the cap 15 as a rigid projection extending to a predetermined level for engaging the intercedent device when it is floating at the predetermined level, and is easily observed for correct filling.

FIG. 6 of the drawings illustrates a modified form of the device having provisions for adding material to the test chamber, or periodically removing materials from the test chamber.

In FIG. 6, the test chamber is designated at 25, and it will be seen that the test chamber 25 has walls 26 which include the conical bottom 28. The upper end 29 of the test chamber 25 is closed by a cap generally designated at 30, the cap 30 defining a central opening 31 which is in the form of a funnel 33 for adding material to the test chamber 25. The funnel 33 can also act as a level gauge like the gauge 22 in FIG. 5.

Surrounding the test chamber 25 is a plurality of peripheral chambers designated at 32. As here shown, it is contemplated that there will be at least four of the peripheral chambers 32, one chamber 32 being on each of four sides of the test chamber 25. For each of the peripheral chambers 32, there is an opening 34 through the wall 26 of the test chamber 25 so that material added to the peripheral chamber 32 can be raised to the height of the opening 34 to cause liquid to flow into the test chamber 25. Conversely, the test chamber 25 can be tipped so that liquid will rise to the level of one of the openings 34 and material will flow from the test chamber 25 into a particular one of the peripheral chambers 32. This arrangement will be discussed in more detail hereinafter.

Looking at FIG. 7 of the drawings, there is again a test chamber generally designated at 35 and having the conical bottom 36 and a cap 38. The test chamber 35 includes an intercedent device 39, the intercedent device 39 being floatable as in the previously described embodiments.

The test chamber 35 is completely enclosed within a sterilizing chamber generally designated at 40. The sterilizing chamber 40 may be generally cylindrical to contain the test chamber 35, and have an appropriate cover 41 for sealing the container 40. In the bottom of the container 40 there may be a dried deposit or compressed mass of a suitable disinfectant 43. While those skilled in the art will suggest many specific disinfectants, lithium hypochlorite will serve quite well for apparatus as disclosed.

With the foregoing discussion of the apparatus in mind, operation of the device should be understandable. As has been previously stated, the general operation of the device is to provide a culture medium within the test chamber, and to add water or the like to be tested, then to provide the desired incubation temperature and the like so that various microbiological forms, if present, will grow sufficiently to reveal their presence. The device of the present invention provides an area X having high oxygen content for growth of aerobic bacteria, an area Y below the first area having a reduced oxygen content for growth of microaerobic bacteria, and an area Z at the bottom of the test chamber having an absence of oxygen for growth of anaerobic bacteria. Also, the intercedent device provides surface area for growth of sessile forms, while the free liquid provides an area for growth of planktonic forms.

The various environments in the test chamber are created in part by the restriction of oxygen diffusion into the environment through the interceptive position of the floating oxygen interceding device 11, and partially by the oxygen-utilizing metabolic activities of the aerobic sessile and planktonic microbial population congregated between the intercedent device 11 and the walls 12 of the culture chamber 10 at the air-liquid interface W. This interface W will extend across the upper surface of the floating intercedent device 11 which is exposed to the air. A biofilm may form over these exposed surfaces, particularly where the device 11 develops a rotational movement on the surface of the liquid.

To achieve a selective function for the apparatus, different concentrates of a specific culture medium may be administered either prior to or during testing. Where prior application is utilized, the sterile medium may be dried on the lower surface 14 of the test chamber 10, or may be administered as a dissolvable, pelletized mass 18, either placed loose within the test chamber, or attached to the floatable intercedent device 11.

In selecting the relative sizes of the intercedent device 11 and the test chamber 10, it will be understood that the distance between the intercedent device 11 and the wall 12 of the test chamber will vary the oxygen activity between the air above the intercedent device 11 and the liquid below the intercedent device by reducing the surface area of liquid exposed to the air and thus reducing the oxygen transfer.

Considering the test chamber as shown in FIG. 1, if a sample of water is to be tested, water will be placed within the test chamber 10, thereby dissolving the dried culture medium 18 and causing the intercedent device 11 to float to the surface of the liquid. The resulting arrangement is shown in FIG. 2 of the drawings. The intercedent device 11 will now intercede the diffusion of oxygen from the atmosphere to the liquid. Diffusion will be restricted to the interface W open zone between the device 11 and the walls 12 of the culture vessel. This site will now be the focus of aerobic activity to the point that the first visual or recordable sign of activity by these organisms occurs at this site. The rapid impeding of oxygen diffusion to the water will cause an encouragement of microaerobic activity, whether sessile or planktonic, in the area Y immediately below the intercedent device 11. As a result, if emphasis is to be placed on the growth of anaerobes, the reduction of oxygen can be accelerated by positioning a biologically inert floating oxygen-impermeable film, such as sterile mineral oil, on the surface of the water between the intercedent device 11 and the wall 12 of the test chamber 10. This will hasten the oxygen removal by the intrinsic aerobic microorganism within the zones X and Y adjacent to the intercedent device 11. The use of the cap 15 will seal the test chamber to prevent inadvertent spillage or contamination of the culture.

In normal circumstances, the culture apparatus will be shipped with the culture medium in a dried state as at 18 in FIG. 1. To complete the apparatus for field usage where conditions are relatively primitive, the culture apparatus may be protected within an outer chamber 40 and capped as by cap 41. The test chamber 35 will be held in position by a disk 42 wherein the apparatus fits into the central hole while the outer edge of the disk conforms closely to the inside diameter of the container 40. A dried deposit or compressed mass of a suitable disinfectant 43 such as lithium hypochlorite may be inside the sterilizing chamber 40 or attached to the disk 42, either through adhesion or within a customized area.

One disposal procedure for the apparatus is therefore to remove the caps 38 and 41, and discharge the contents of the test chamber 35 into the chamber 40. Both the floating intercedent device 39 and the cap 38 will be placed into the chamber 40, and the chamber 40 will be capped again with the closure device 41. Disinfectant emanating from the attached disinfecting material 43 will dissolve and, over time, disinfect the organisms in the liquid matrix.

Adjustments in the design of the culture apparatus can allow an improvement in the ability of the device to monitor specific groups of microorganisms. The provision of the shelf 13 shown in FIG. 3 just below water level will cause the water to expand over the surface area as a thin layer 15 and provide a larger and more visible area W for intense aerobic microbial activity.

Where a prime objective is to determine the presence of any evolved insoluble or supersaturated gas products, the design of the floating intercedent device can be modified as shown in FIG. 4 to allow a large area of close proximity between the wall 12 and the device 11B. The parallel sides lie in close proximity to the inner walls of the chamber, and gas bubbles will become visibly entrapped within the confines of this zone. It has been observed that some types of gas also will produce adhered bubbles on the lower side of the floating intercedent device when the device is either spherical or as shown in FIG. 4.

Where it is apparent that a number of test are required to be conducted simultaneously on the aerobic sessile and planktonic microorganisms, the role of the intercedent device 37 can be modified to cause the device to impede and control the flow of the liquid sample into a number of peripherally defined chambers 32 into which sample liquid will flow slowly through ports while being controlled by the device 37. The position of the device 37 is restricted by either an open cone 33 or rod 22 so that, when the device comes into line with one of the openings 34 it will cause sample material to enter the individually defined chambers 32. By slowly rotating the apparatus, and at the same time tilting the axis to approximately 40° from the vertical, water will be admitted to each of the chambers 32 in turn to initiate a separate testing. A reverse pattern may be initiated wherein the device 37 controls the admission of liquid to the main chamber 25 through the openings 34.

A principal object of the present invention is to provide a manual, low load field or laboratory system to act as a primary qualitative or semi-quantitative screen prior to optional, more detailed, laboratory studies. Practice of this invention contemplates making the test results (automated or manual) comparable to graphically presented standards along with tables and descriptors where required. Users will be encouraged to undertake comparable controls.

Since the microbial activity tests are designed around the apparatus of the present invention, there is a common sequence of the application to which variations are applied. The sample is applied above the floating intercedent device which may or may not be supported on a liquid. When applied, the targeted microorganisms shall be encouraged to metabolize and grow through the selective nature of the chemicals supplemented into the liquid from a concentrate. Any oxygen-utilizing activity generated by the sessile and planktonic microorganisms at the space between the intercedent device and the inner walls of the chamber will retard the diffusion of oxygen into the liquid and consequently accelerate the establishment of an oxygen-free environment within which anaerobic microorganisms can florish. The various test methods employ a different set of metabolic and growth reactions which occur within one or more of these differentiating aerobic and anaerobic zones.

For conducting a test, the protective cap 15 is removed, or the delivery/positioning funnel outer orifice 31 exposed. In the former case, the prescribed sample is placed into the tube. In the latter case, a defined volume of the liquid sample is administered to the delivery/positioning funnel 33 through the opening 31 to cause the intercedent device to elevate to the point of coming into physical contact with the lower open end of the funnel 33. This event causes the air above the liquid to compress and, together with the physical restriction of the intercedent device 37 prevents further liquid sample from entering the chamber 25. In both formats, the floating intercedent device is positioned at the predesignated site within the apparatus. Chemicals, nutrients, differential and selective agents can now diffuse throughout the liquid to provide an appropriate environment for the evaluation process. This process of evaluation involves the placement of the apparatus in conditions of temperature and light considered appropriate to the development of the defined reaction patterns. After this development, or incubation, period, the apparatus is examined for any of the diagnostic characteristics associated with the targeted microbial group. Successive development periods may follow in an ongoing program of monitoring in order to achieve a semi-quantitative evaluation of the sample.

As can be seen from the foregoing description, the present invention requires the characterization of some element of growth or activity within the apparatus to complete an evaluation. By way of example, the following characteristics may indicate the causes listed:

| Characteristics | Cause |
| --- | --- |
| Blackening | Sulfide deposition |
| Turbidity | Microbial planktonic growth |
| Turbidity adjacent to intercedent device in area X | Aerobic planktonic growth |
| Turbidity below intercedent device in area Z | Anaerobic planktonic growth |
| Swirling turbidity at the bottom of chamber rising to area adjacent to intercedent device upon vigorous rotation. | Extracellular polymer substance producing microbes, slime |
| Discoloration and/or coating of the floating intercedent device | Sessile aerobe microbial colonization |
| Adhered patches of colored deposits on the wall of test chamber just below intercedent device | Microaerobic colony formation |
| Black deposit in chamber below bottom attached to lower inner walls of bottom. | Sulfide deposits originating from microbially generated hydrogen sulfide |
| Defined gas bubbles either entrapped adjacent to intercedent device or adhering to the underside of the intercedent device | Microbially generated insoluble or supersaturated soluble gases |
| Differential color changes between areas adjacent to intercedent device, just below intercedent device and at bottom | Relative activity of the aerobic, microaerobic and anaerobic flora |
| Green color generation | Micro-algal growth |
| Brown color generation | Iron related bacterial growth |
| U.V. fluorescing zone | Microbially generated U.V. fluorescent soluble or insoluble pigment |

Although the reagents and culture media form no part of the present invention, the widespread application of the apparatus and procedures described above is noteworthy. The following are examples of the bacterial activity tests that can be carried out herewith:

Iron Related Bacterial (IRB-BAT)
Sulfur Reducing bacteria (SURB-BAT)
Pseudomonads (SPE-BAT)
Algae (green) (LGG-BAT)
Algae (blue green cyanobacterial) (LCG-BAT)
Black Plug Layer Generation Potential (BPL-BAT)
Methanogens (MET-BAT)
Coliforms (COL-BAT)
Streptomyces (STR-BAT)

Each of the above test systems achieves its uniqueness in function by the application of specific chemicals and culture media in an environment wherein the floating intercedent device provides a surface for sessile growth and a restricted planktonic zone for aerobic microbial activities.

It will of course be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as outlined in the appended claims.

We claim:

1. A test apparatus for determining the presence of selected microorganisms in a given sample, said test apparatus comprising a test chamber having a bottom area, a central area, and an open top, a cover for selectively closing said open top, and a floatable intercedent device within said test chamber, a quantity of liquid within said test chamber, said quantity of liquid including a culture medium for promoting growth of selected microorganisms and said given sample, said intercedent device being floatable generally at the surface of said quantity of liquid, said intercedent device being of such size and shape as to substantially block said test chamber for inhibiting transfer of oxygen from the atmosphere above said intercedent device to said liquid below said intercedent device, the arrangement being such that said intercedent device in conjunction with said microorganisms reduces oxygen transfer to the area below said intercedent device for providing an area of diminished oxygen content.

2. A test apparatus as claimed in claim 1, and wherein said selected microorganisms consist of anaerobic bacteria, said test apparatus further including an air impermeable medium covering the surface of said liquid for preventing oxygen transfer from the atmosphere above said intercedent device into said liquid.

3. A test apparatus as claimed in claim 1, wherein said bottom area of said test chamber has a smaller periphery than said top of said test chamber for defining a shelf in said central area, said liquid filling said test chamber to a point above said shelf for providing a larger surface of said liquid for increased transfer of oxygen into said liquid.

4. A test apparatus as claimed in claim 1, wherein said floatable intercedent device is generally spherical and has about half the surface immersed in said liquid for providing a surface for growth of sessile microorganisms.

5. A test apparatus as claimed in claim 1 wherein said floatable intercedent device includes a generally cylindrical portion, the sides of said generally cylindrical portion being disposed parallel to the walls of said test chamber for providing a gas collection area.

6. A test apparatus as claimed in claim 1, and including indicating means for indicating the level of liquid in said test chamber, said indicating means including a rigid projection from said cover extending to a predetermined level for engaging said intercedent device when said intercedent device is floating at said predetermined level.

7. A test apparatus as claimed in claim 6, and further including at least one peripheral chamber contiguous with said test chamber, said test chamber having an opening therein for allowing communication between said test chamber and said peripheral chamber.

8. A test apparatus as claimed in claim 1, and further including a sterilizing container, said sterilizing container having a height sufficient to receive said test chamber therein, and a diameter larger than said test chamber, disinfecting means within said sterilizing container, and sealing means for closing said sterilizing container sufficiently to prevent leakage therefrom.

9. A method of testing to determine the presence of selected microorganisms, including the step of placing a sample to be tested into a container, providing a culture medium for said selected microorganisms in a liquid within said container, floating an intercedent device generally on the surface of the liquid within said container for dividing said container, said intercedent device being of such size and shape as to reduce the surface area of said liquid exposed to the atmosphere above said liquid for reducing the oxygen transfer from above said intercedent device to below said intercedent device for providing a first area of the liquid adjacent to said intercedent device having sufficient oxygen content for growth of aerobic microorganisms, a second area of the liquid below said intercedent device having a reduced oxygen content for growth of microaerobic microorganisms, and a third area of the liquid adjacent to the bottom of said container substantially devoid of oxygen for growth of anaerobic microrganisms.

* * * * *